(12) United States Patent
Chin et al.

(10) Patent No.: US 9,801,732 B2
(45) Date of Patent: Oct. 31, 2017

(54) SYSTEM AND METHOD FOR AN INTERVERTEBRAL IMPLANT ASSEMBLY

(75) Inventors: Kingsley Chin, Hallendale, FL (US);
Vito Lore, Somerville, MA (US);
Michael Drnek, Boston, MA (US);
Christopher Chang, Beverly, MA (US)

(73) Assignee: SPINEFRONTIER, INC, Malden, MA (US)

( * ) Notice: Subject to any disclaimer, the term of this patent is extended or adjusted under 35 U.S.C. 154(b) by 1849 days.

(21) Appl. No.: 12/913,004

(22) Filed: Oct. 27, 2010

(65) Prior Publication Data
US 2011/0106261 A1    May 5, 2011

Related U.S. Application Data

(60) Provisional application No. 61/256,435, filed on Oct. 30, 2009.

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/3008* (2013.01); *A61F 2002/3082* (2013.01); *A61F 2002/3092* (2013.01); *A61F 2002/30131* (2013.01); *A61F 2002/30135* (2013.01); *A61F 2002/30904* (2013.01); *A61F 2002/4475* (2013.01); *A61F 2002/4627* (2013.01)

(58) Field of Classification Search
USPC ...................... 606/246–249, 99, 86 A, 86 R; 623/17.11–17.16
See application file for complete search history.

(56) References Cited

U.S. PATENT DOCUMENTS

| 4,904,261 | A | | 2/1990 | Dove et al. |
| 5,676,146 | A | | 10/1997 | Scarborough |
| 5,885,299 | A | * | 3/1999 | Winslow et al. ............... 606/99 |

(Continued)

FOREIGN PATENT DOCUMENTS

FR    WO2005032432 A1    4/2005

*Primary Examiner* — Matthew Lawson
(74) *Attorney, Agent, or Firm* — AKC Patents, LLC; Aliki K. Collns

(57) ABSTRACT

An intervertebral implant assembly includes and inserter tool and an implant having a U-shaped body shaped and dimensioned to be placed between two adjacent vertebras. The U-shaped body comprises a rounded front end, an open back end, first and second elongated components extending from the rounded front end, forming the U-shaped body and ending at the open back end and at least one rigid strut extending from and connecting opposite inner side surfaces of the first and second elongated components. A first through-opening is formed in the space between the front end, the rigid strut and the opposite inner side surfaces of the front portions of the first and second elongated components and a second through-opening is formed in the space between the open back end, the rigid strut and the opposite inner side surfaces of the back portions of the first and second elongated components. The inserter tool comprises a shaft, a middle sleeve and an outer sleeve that work together to attach and lock to the implant.

11 Claims, 11 Drawing Sheets

(56) References Cited

U.S. PATENT DOCUMENTS

| | | |
|---|---|---|
| 6,319,257 B1 * | 11/2001 | Carignan et al. ............... 606/99 |
| 6,482,233 B1 | 11/2002 | Aebi et al. |
| 6,511,509 B1 | 1/2003 | Ford et al. |
| 6,530,955 B2 | 3/2003 | Boyle et al. |
| 6,558,424 B2 | 5/2003 | Thalgott |
| 7,018,416 B2 | 3/2006 | Hanson et al. |
| 7,232,463 B2 | 6/2007 | Falahee |
| 7,294,134 B2 | 11/2007 | Weber |
| 7,303,583 B1 | 12/2007 | Schar et al. |
| 7,727,280 B2 | 6/2010 | McLuen |
| 8,623,088 B1 * | 1/2014 | Tohmeh ............... A61F 2/4455 623/17.11 |
| 2002/0177897 A1 * | 11/2002 | Michelson ................ 623/17.11 |
| 2004/0267275 A1 | 12/2004 | Cournoyer et al. |
| 2006/0129238 A1 * | 6/2006 | Paltzer .................... A61F 2/447 623/17.11 |
| 2006/0200166 A1 * | 9/2006 | Hanson et al. ............... 606/99 |
| 2006/0253201 A1 | 11/2006 | McLuen |
| 2007/0050031 A1 | 3/2007 | Khosrowshahi |
| 2008/0154377 A1 * | 6/2008 | Voellmicke ............... 623/17.16 |
| 2010/0204796 A1 | 8/2010 | Bae et al. |

* cited by examiner

US 9,801,732 B2

SYSTEM AND METHOD FOR AN INTERVERTEBRAL IMPLANT ASSEMBLY

CROSS REFERENCE TO RELATED CO-PENDING APPLICATIONS

This application claims the benefit of U.S. provisional application Ser. No. 61/256,435 filed Oct. 30, 2009 and entitled "SYSTEM AND METHOD FOR MEDIAL/LATERAL LUMBAR FUSION", the contents of which are expressly incorporated herein by reference.

FIELD OF THE INVENTION

The present invention relates to a system and a method for an intervertebral implant assembly, and more particularly to the use of an intervertebral implant for decompression and fusion.

BACKGROUND OF THE INVENTION

The human spine includes individual vertebras that are connected to each other. Under normal circumstances the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal, achieve stability, protect the neural structures, or to relief the patient of discomfort. The goal of spine surgery for a multitude of spinal disorders especially those causing compression of the neural structures is often decompression of the neural elements and/or fusion of adjacent vertebral segments. Fusion works well because it stops pain due to movement at the facet joints or intervertebral discs, holds the spine in place after correcting deformity, and prevents instability and or deformity of the spine after spine procedures such as discectomies, laminectomies or corpectomies. Discectomy and fusion are commonly performed in the cervical spine but there is increasing application in the thoracic and lumbar spine, as well.

Several spinal fixation systems exist for stabilizing the spine so that bony fusion is achieved. The majority of these fixation systems utilize fixation elements such as rods wires or plates that attach to screws threaded into the vertebral bodies, facets or the pedicles. In addition to stabilization of the vertebral elements with fixation elements, there is a need to maintain the decompression of the intervertebral discs where discectomies or microdiscectomies have been performed. Some of theses decompression methods include inserting an implant in the intervertebral space between two adjacent vertebras in order to maintain the desired axial distance from the superior and inferior vertebral wall. The intervertebral implant is usually made of a biocompatible material in the shape of a hollow block. The intervertebral implant may be inserted from the anterior, posterior, from a transforaminal approach, or medial/lateral approach. In other decompression methods, bone growth material such as bone graft, harvested bone, or dematerialized bone matrix are injected, inserted, or impacted into the disc space. This material fills the space remaining from the discectomy procedure and acts as a catalyst for bone growth and bone fusion within the disc space.

The use of stabilization rods in combination with the insertion of an intervertebral implant is effective in treating several spinal disorders. However, the operating procedure for attaching the rods and inserting the intervertebral implant is usually long. Accordingly, it is desirable to provide an intervertebral implant that offers both stabilization and decompression of adjacent vertebras.

SUMMARY OF THE INVENTION

The invention relates to a system and method for an intervertebral implant assembly that includes a U-shaped implant and a unique inserter, which attaches to the implant without the use of threads or screws through the implant. Once in the body, the implant acts as a spacer for intervertebral decompression and promotes vertebral fusion with the use of bone growth materials.

In general, in one aspect, the invention features an intervertebral implant assembly for stabilization and decompression of two adjacent spinal vertebras including an implant having a U-shaped body shaped and dimensioned to be placed between two adjacent vertebras. The U-shaped body comprises a rounded front end, an open back end, first and second elongated components extending from the rounded front end, forming the U-shaped body and ending at the open back end and at least one rigid strut extending from and connecting opposite inner side surfaces of the first and second elongated components. A first through-opening is formed in the space between the front end, the rigid strut and the opposite inner side surfaces of the front portions of the first and second elongated components and a second through-opening is formed in the space between the open back end, the rigid strut and the opposite inner side surfaces of the back portions of the first and second elongated components.

Implementations of this aspect of the invention may include one or more of the following features. First and second grooves are formed on the outer side surfaces of the back portions of the first and second elongated components. The first and second grooves start at the back end and terminate at the mid-section of the outer side surfaces of the first and second elongated components, respectively. The top and bottom surfaces of the U-shaped body comprise protrusions configured to grip into the bottom and top surfaces of the two adjacent vertebras, respectively. The top and bottom surfaces of the U-shaped body are inclined and taper from the back side toward the front side. The U-shaped body further comprises holes extending from the top surface to the bottom surface and pins dimensioned to fit within the holes. The pins comprise radio-opaque material and are used as position indicators during fluoroscopy. Bone growth material is inserted in the first and second through openings. The first and second elongated components comprise first and second extensions, extending from and being perpendicular to the back ends of the first and second elongated components, respectively. The first and second extensions protrude inward and do not converge together. The first extension comprises a first rectangular portion at the bottom, a rounded portion in the middle and a second rectangular portion at the top. The second rectangular portion is set outward at a plane parallel to the first rectangular portion. The second extension comprises a first rectangular portion at the top, a rounded portion in the middle and a second rectangular portion at the bottom. The second rectangular portion is set outward at a plane parallel to the first rectangular portion. The assembly further includes an inserter tool. The inserter tool comprises an elongated inner shaft comprising a flat disc at the distal end, a middle sleeve surrounding the elongated shaft and comprising an attachment jaw at its distal end and an L-shaped opening at its proximal end, and an outer sleeve surrounding the middle sleeve. The flat disc comprises first and second protrusions extending from the sides of the flat disc. The first and second protrusions are configured to be inserted in the open back end of the U-shaped body and to be placed behind the first and second extensions of the U-shaped body, respectively. The elongated inner shaft further comprises a pin at its proximal end. The pin is shaped and dimensioned to be inserted and rotated within the L-shaped opening of the middle sleeve. The elongated inner shaft further comprises a spring-loaded ball and the middle sleeve comprises first and second detent holes dimensioned to capture the spring loaded ball. The attachment jaw comprises first and second protrusions shaped and dimensioned to slide within the first and second grooves of the U-shaped body, respectively. The first and second protrusions comprise ridges on their inner surfaces. The outer sleeve comprises inner threads and the middle sleeve comprises outer threads. The outer sleeve inner threads are configured to engage the outer threads of the middle sleeve and thereby to move the outer sleeve partially over the attachment jaw and thereby to lock the first and second protrusions in place.

In general in another aspect the invention features an inserter tool including an elongated inner shaft comprising a flat disc at the distal end, a middle sleeve surrounding the elongated shaft and comprising an attachment jaw at its distal end and an L-shaped opening at its proximal end and an outer sleeve surrounding the middle sleeve. The elongated inner shaft further comprises a pin at its proximal end and the pin is shaped and dimensioned to be inserted and rotated within the L-shaped opening of the middle sleeve. The inserter tool is used for grasping and inserting an intervertebral implant.

Implementations of this aspect of the invention may include one or more of the following features. The elongated inner shaft further comprises a spring-loaded ball and the middle sleeve comprises first and second detent holes dimensioned to capture the spring loaded ball. The intervertebral implant comprises a U-shaped body shaped and dimensioned to be placed between two adjacent vertebras, and the U-shaped body comprises a rounded front end, an open back end, first and second elongated components extending from the rounded front end, forming the U-shaped body and ending at the open back end and at least one rigid strut extending from and connecting opposite inner side surfaces of the first and second elongated components. The flat disc comprises first and second protrusions extending from the sides of the flat disc and the first and second protrusions are configured to be inserted in the open back end of the U-shaped body of the intervertebral implant and to be placed behind the first and second extensions of the U-shaped body, respectively. The attachment jaw comprises first and second protrusions shaped and dimensioned to slide within first and second grooves of the U-shaped body, respectively. The first and second protrusions comprise ridges on their inner surfaces. The outer sleeve comprises inner threads and the middle sleeve comprises outer threads and the outer sleeve inner threads are configured to engage the outer threads of the middle sleeve and thereby to move the outer sleeve partially over the attachment jaw and thereby to lock the first and second protrusions in place.

In general in another aspect the invention features a method for stabilizing and decompressing two adjacent spinal vertebras, including inserting an implant between two adjacent vertebras. The implant comprises a U-shaped body having a rounded front end, an open back end, first and second elongated components extending from the rounded front end, forming the U-shaped body and ending at the open back end and at least one rigid strut extending from and connecting opposite inner side surfaces of the first and second elongated components. The implant further comprises a first through-opening formed in the space between the front end, the rigid strut and the opposite inner side surfaces of the front portions of the first and second elongated components, and a second through-opening formed in the space between the open back end, the rigid strut and the opposite inner side surfaces of the back portions of the first and second elongated components. The method also includes inserting bone growth material in the first and second through openings.

Among the advantages of this invention may be one or more of the following. The inserter attaches to the implant without the use of threads or screws through the implant. Once in the body, the implant acts as a spacer for intervertebral decompression and promotes vertebral fusion with the use of bone growth materials. Bone growth material can be inserted in the second through opening through the open back end after the implant has been inserted between the adjacent vertebras.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1:
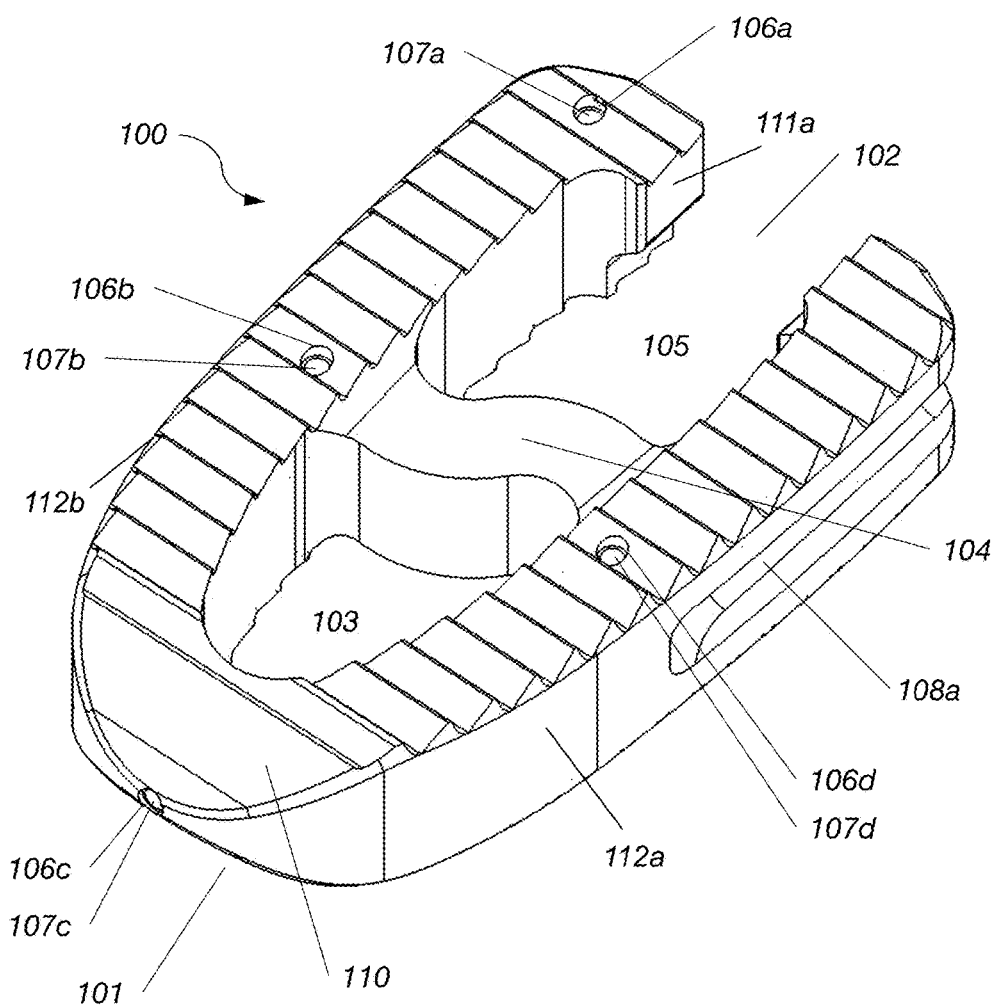
FIG. 1 is a top perspective view of the intervertebral implant.
Figure 2:
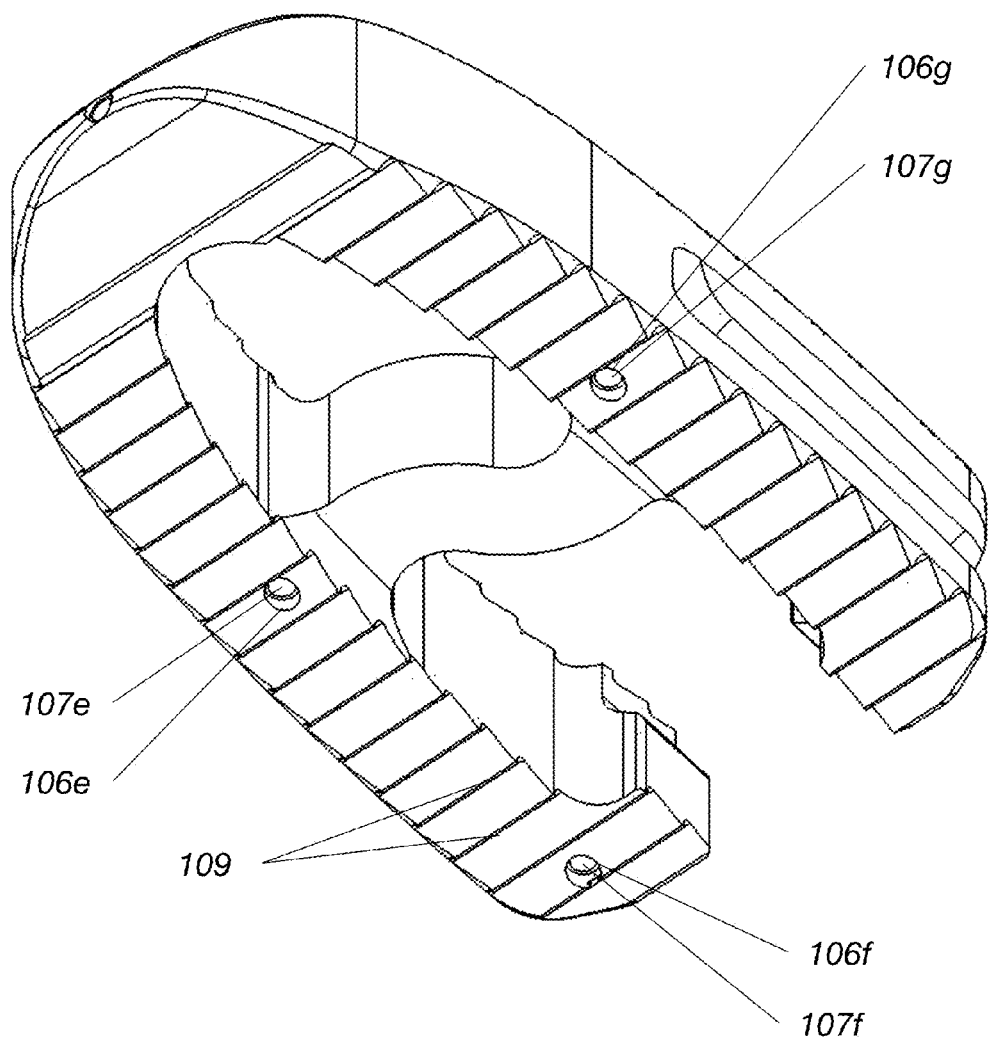
FIG. 2 is a bottom perspective view of the intervertebral implant.
Figure 3:
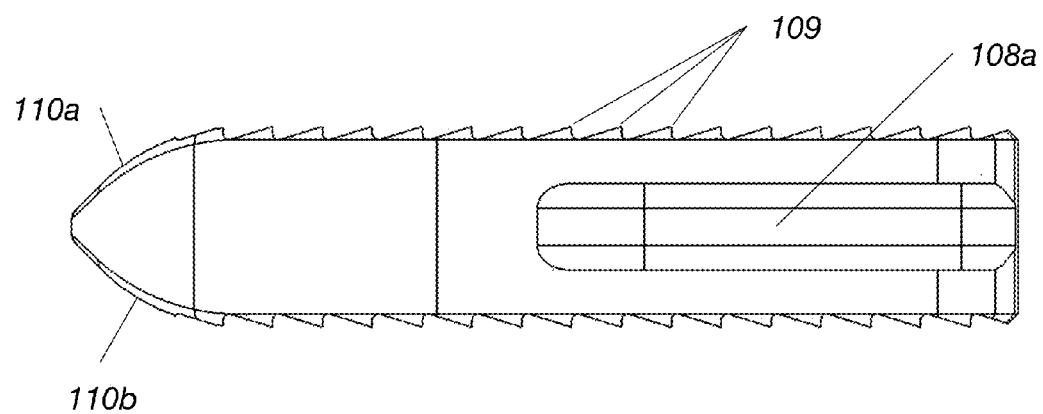
FIG. 3 is a side view of the intervertebral implant of FIG. 1.
Figure 4:
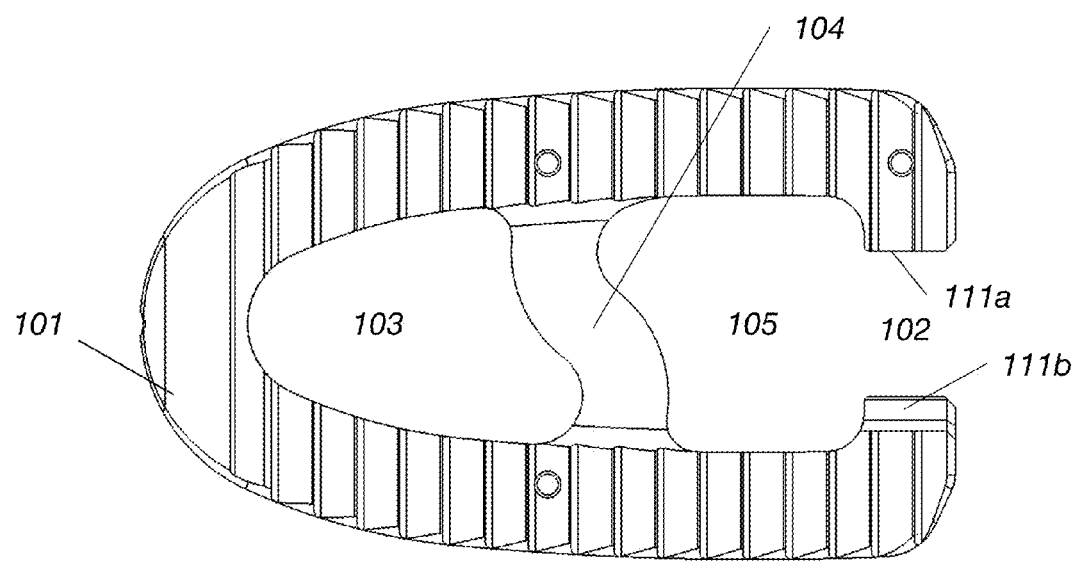
FIG. 4 is a top view of the implant of FIG. 1.
Figure 5:
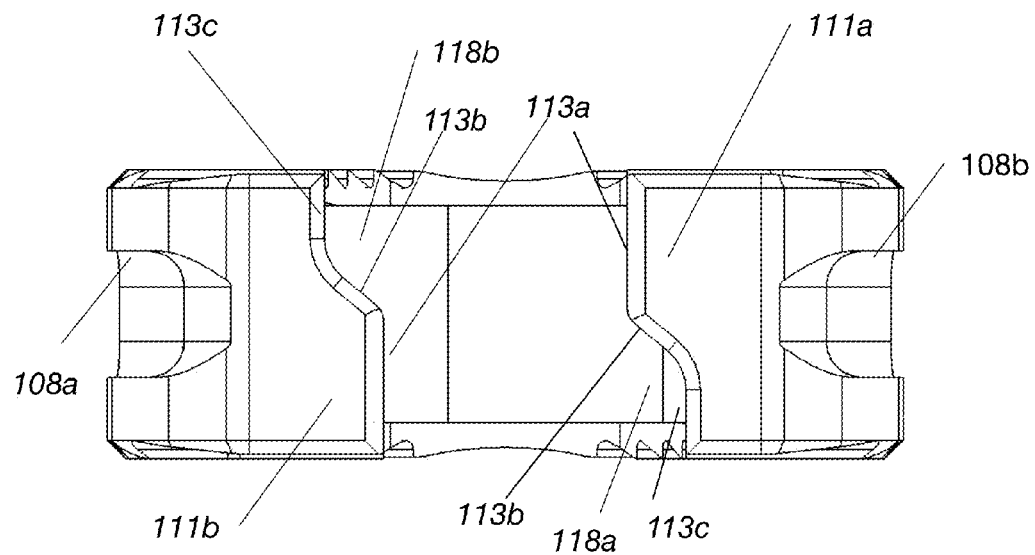
FIG. 5 is a rear view of the implant of FIG. 1.
Figure 6:
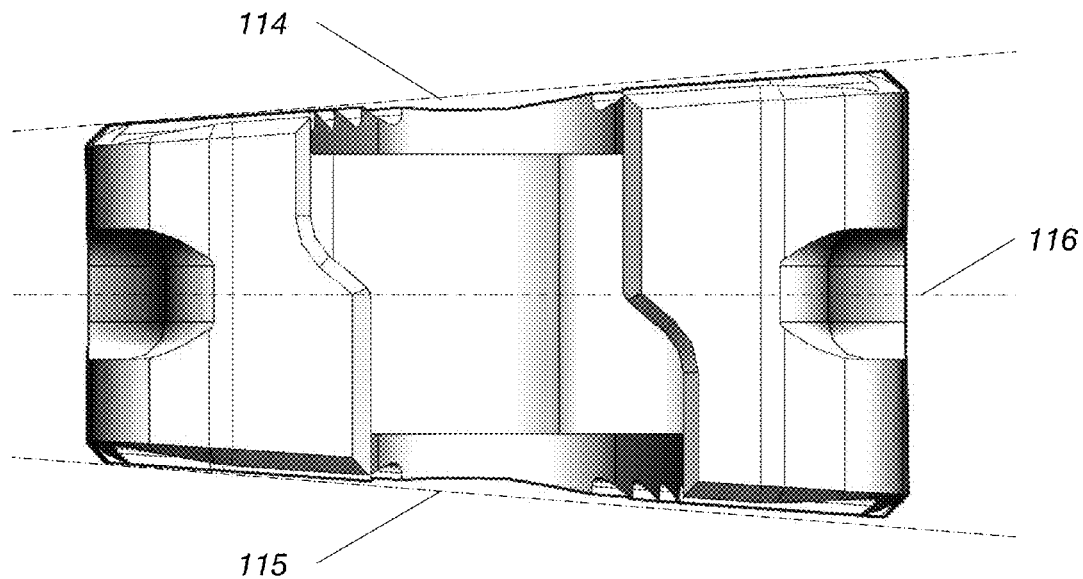
FIG. 6 shows a rear view of another embodiment of the intervertebral implant.
Figure 7:
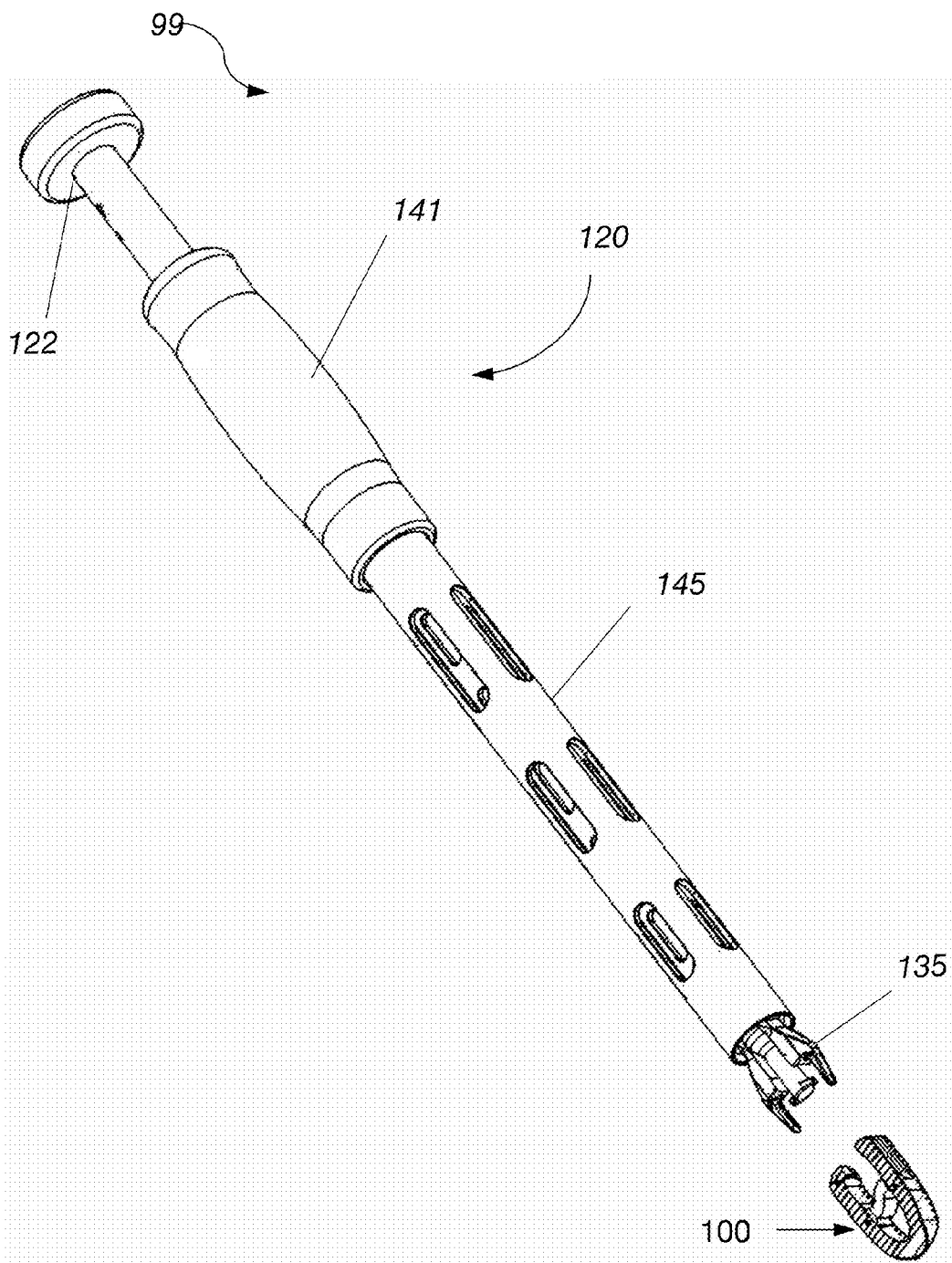
FIG. 7 shows the intervertebral implant assembly with the inserter tool.
Figure 8:
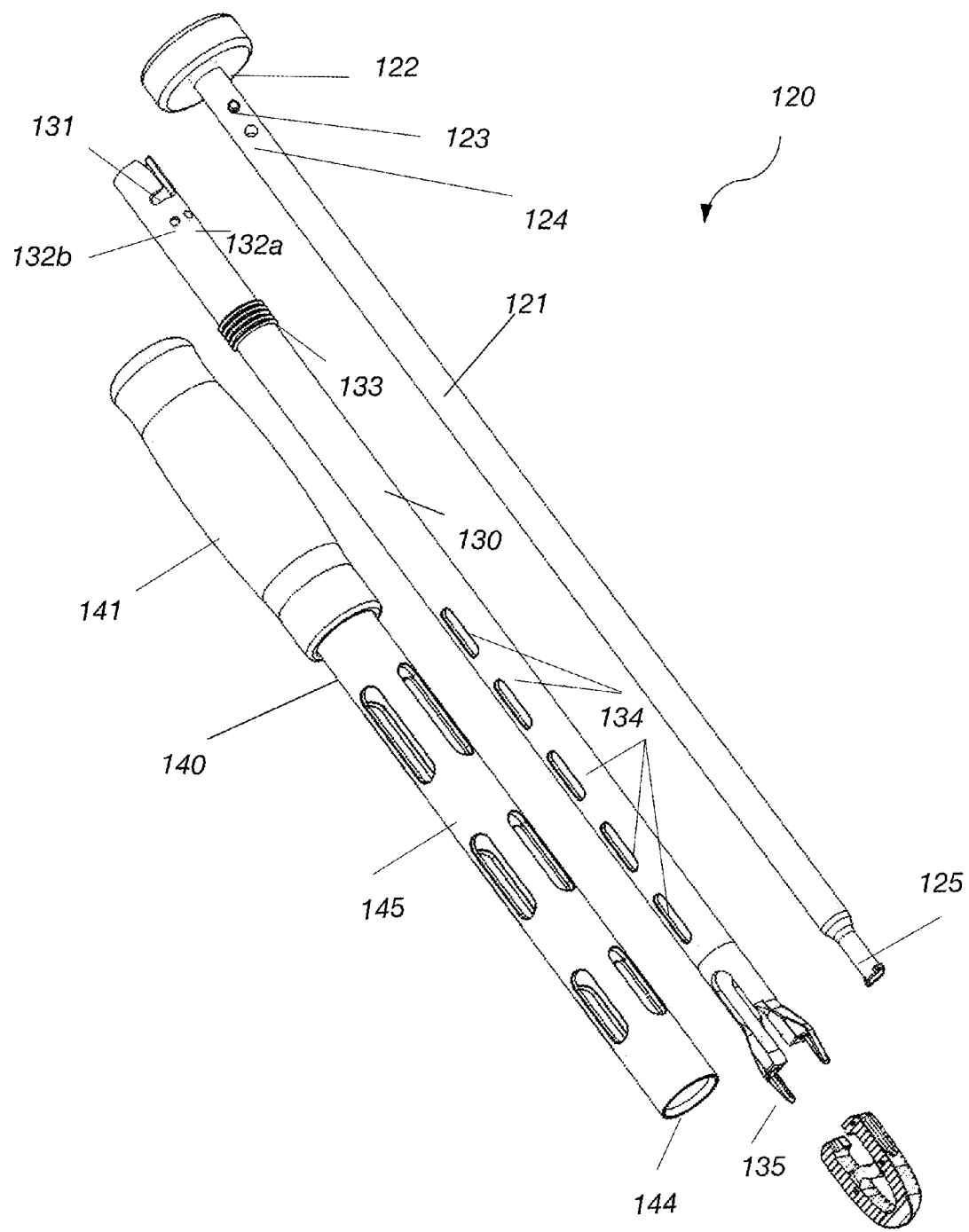
FIG. 8 is an exploded view of the inserter tool of FIG. 7.

Referring to FIG. 7, implant assembly 99 includes an interbody implant 100 used for spinal fusion procedures and a unique inserter 120, which attaches to the implant 100 without the use of threads or screws through the implant. Referring to FIG. 1-5, implant 100 includes a "U" shaped body 110 having two elongated members 112a, 112b connecting at the rounded front end 101 and being open at the back end 102. The implant 100 is made of biocompatible materials that are either porous or non-porous in texture. There are one or more openings 103, 105 in the middle of the implant 100, which are separated by one or more rigid struts 104. Struts 104 connect the inner sides of the "U" shaped body 110. In this embodiment, struts 104 have an "S" shape form. In other embodiments, struts 104 may be straight, cylindrical, or curved. Openings 103, 105 are used for holding compacted bone growth materials. The opening 105 at the backside of the implant 100 is open at the back end 102. This open end 102 provides the option of inserting bone growth material into the opening 105 after the implant 100 has been inserted in the intervertebral space. Throughout the top, bottom, and front surfaces are a multitude of holes 106a-106g, which are shaped and dimensioned to receive cylindrical shaped pins 107a-107g. These pins 107a-107g are made of a biocompatible radio-opaque material and are used as markers for determining position and orientation of the implant 100 during fluoroscopy. On both sides of the implant 100 there are grooves 108a, 108b that start at the back end and terminate at the mid-section of each side. Grooves 108a, 108b are used for receiving, aligning and fixing the inserter tool 120 onto the implant 100. On the top and bottom sides of the implant are ridges 109 with pointed peaks for gripping into the adjacent vertebras 90a, 90b and preventing expulsion from the intervertebral disc space, shown in FIG. 17b. The top and bottom surfaces 110a, 110b taper inward toward the front end 101 and meet together at the front end 101 thereby creating a tapered front. This tapered front acts as a wedge during insertion into the intervertebral disc space. At the opening of the back end 102 are two extensions 111a and 111b that protrude inward but do not converge together. Referring to FIG. 5, extension 111b has a rectangular shaped vertical wall 113a that starts at the bottom and is angled at the top of the rectangle. This angled top 113b rounds to another rectangular shaped vertical wall 113c that is parallel to wall 113a and is set outward relative to vertical wall 113a and it extends up to the top surface. Extension 111a also has a rectangular shaped vertical wall 113a that starts at the top and is angled at the bottom of the rectangle. This angled bottom 113b rounds to another rectangular shaped vertical wall 113c that is parallel to wall 113a and is set outward relative to vertical wall 113a and it extends down to the bottom surface of the implant. These extensions 111a, 111b are used for locking the implant 100 onto the inserter 120 via a twist locking mechanism, as will be described below. In one example, implant 110 has a length in the range of 38-58 mm, a width of 22 mm and a height in the range of 8-16 mm. In another embodiment, the implant includes an angled top 114, and an angled bottom, 115, as shown in FIG. 6. In this embodiment, the top and bottom surfaces are equally angled from midline 116. In other embodiments, top and bottom surfaces are not equally angled from the midline 116. In other embodiments, strut 104 has a height smaller than the height of the implant 110.

Figure 9:
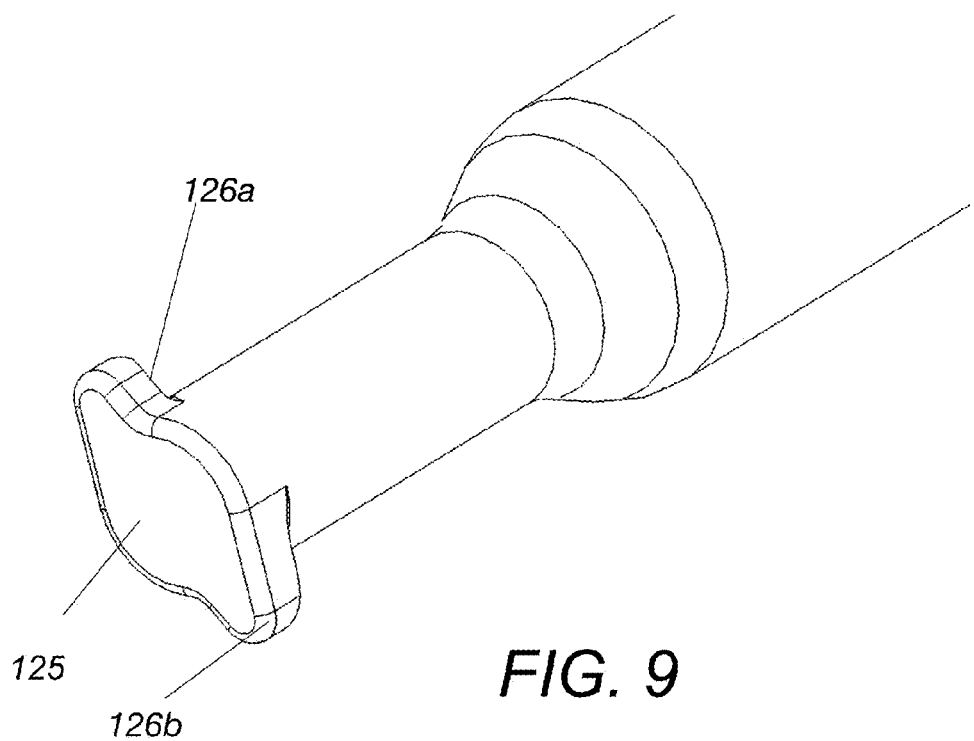
FIG. 9 shows a detailed view of the distal end of the inner shaft of FIG. 8.
Figure 10A:
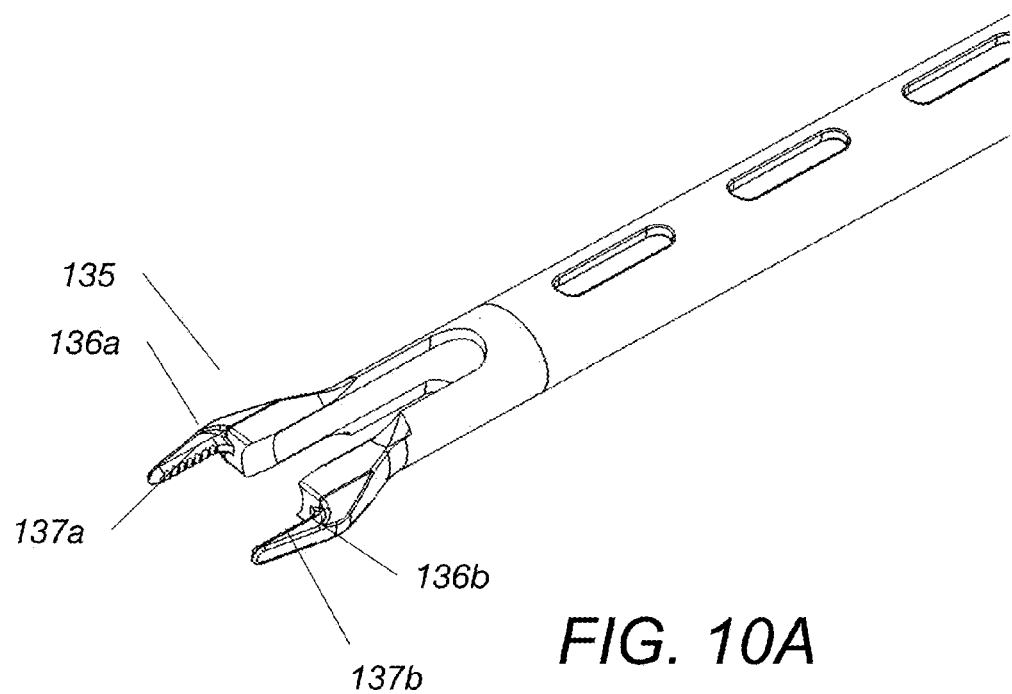
FIG. 10a shows a detailed view of the distal end of the middle sleeve of FIG. 8.
Figure 10B:
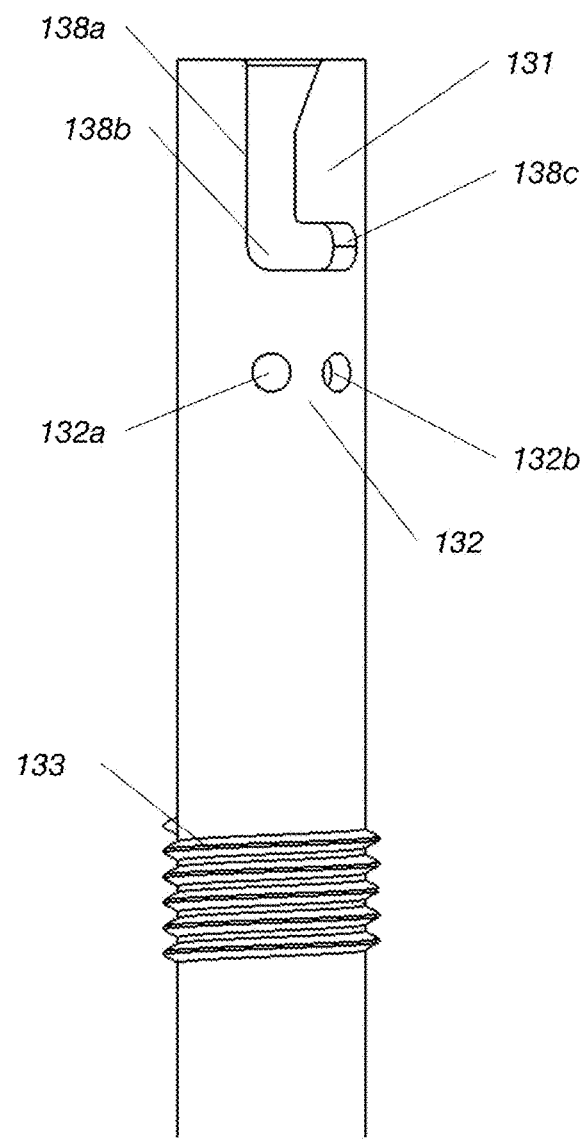
FIG. 10b shows a detailed view of the proximal end of the middle sleeve of FIG. 8.
Figure 11:
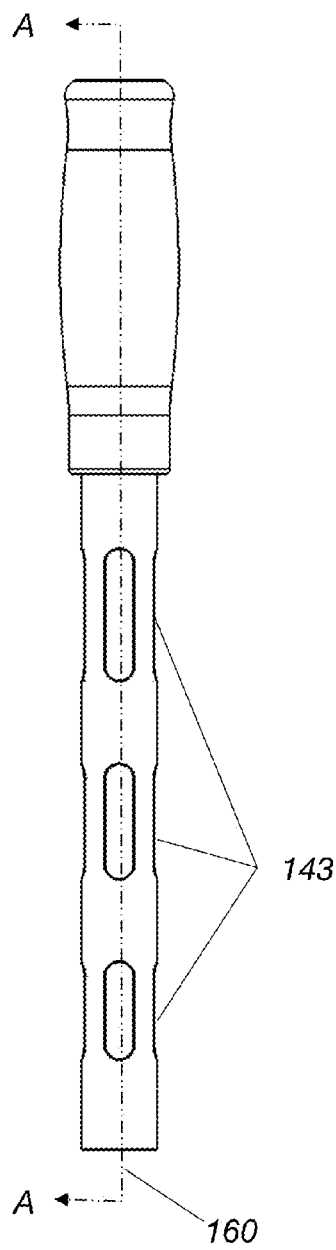
FIG. 11 shows a front view of the outer sleeve on FIG. 8.
Figure 12:
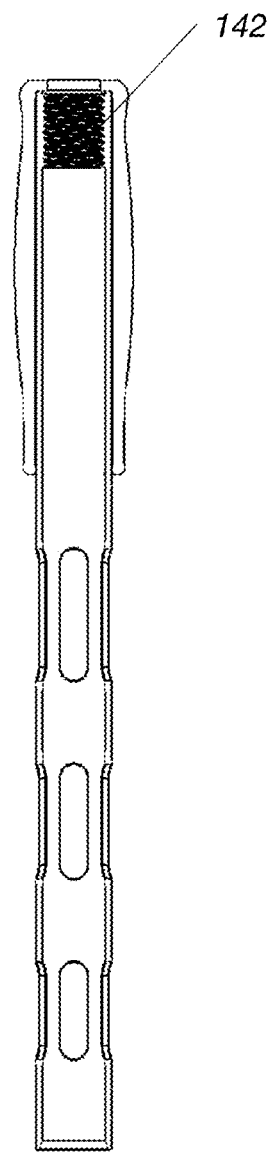
FIG. 12 shows a cross-sectional view of the outer sleeve along line 160 of FIG. 11.
Figure 13:
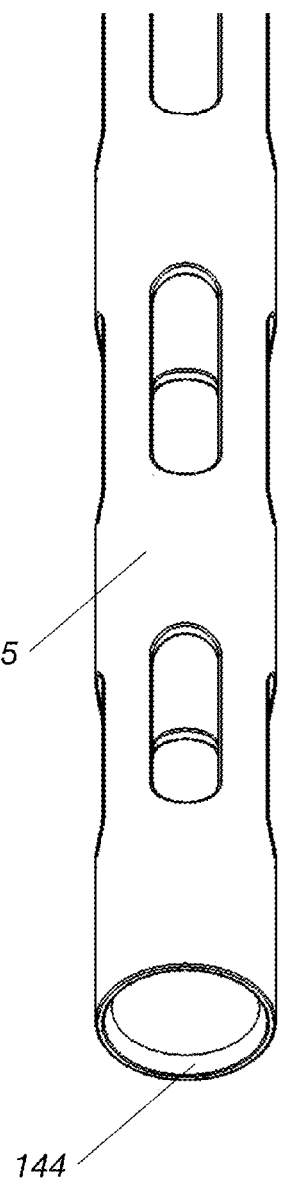
FIG. 13 shows a detailed view of the distal end of the outer sleeve of FIG. 11.

Referring to FIG. 7-13, the inserter tool 120 includes an inner shaft 121, a middle sleeve 130 and an outer sleeve 140. Middle sleeve 130 surrounds the inner shaft 121 and outer sleeve 140 surrounds the middle sleeve 130. Inner shaft 121 includes a strike plate 122 at the proximal end and a flat disc 125 at the distal end. Flat disc 125 includes protrusions 126a and 126b that extend from the sides of the disc, as shown in FIG. 9. Inner shaft 121 also includes a pin or notch 123 protruding from the shaft just below the strike plate 122 and a spring-loaded ball 124. As will be described below, pin 123 is inserted in an L-shaped opening 131 of the middle sleeve 130 and the spring-loaded ball 24 is captured into detent holes 132a or 132b of the middle sleeve. To attach the implant 100 onto the inserter 120, the flat disc 125 is inserted into the back opening 102 of the implant 100 and protrusions 126a, 126b of the disc 125 slide into openings 118a, 118b of the implant 100. To lock the implant 100 onto the inner shaft 121, the disc 125 is rotated counter-clockwise by 90 degrees, and the protrusions 126a, 126b are placed behind the vertical walls 113a of extensions 111a and 111b of the back end of the implant 102. The disc 125 is rotated by first pushing the spring-loaded ball 24 inward and then rotating the inner shaft 121 counter-clockwise by a quarter turn until the spring-loaded ball 124 moves into detent hole 132b in the middle sleeve 130.

Middle sleeve 130 includes attachment jaws 135 at its distal end and the above mentioned L-shaped opening 131 and detent holes 132a, 132b at the proximal end. The attachment jaws 135 include two opposite and equal protrusions 136a and 136b with ridges 137a and 137b on their inner surfaces. Protrusions 136a and 136b slide into grooves 108a, 108b formed in the outer sides of implant 100 and ridges 137a, 137b grip onto the outer side surfaces of implant 100. Pin 123 of the inner shaft 121 travels down the vertical channel 138a of the L-shaped opening and rests at the mid-corner 138b, while spring-loaded ball 124 is captured in detent hole 134a in the implant unlocked position 151. In the implant locked position 153, the pin 123 is turned and sits at the end 138c of the L-shaped opening 131 and the spring loaded ball 124 is captured in detent hole 134b. The L-shaped opening 131, detent-hole mechanism 132, disc 125 with protrusions 126a, 126b and extensions 111a, 111b of the implant 100 all work together to lock the implant 100 onto the inserter 120 and to prevent distal/proximal motion. There are also a series of threads 133 below the detent-hole mechanism 132, which interface with threads in the outer sleeve 140, as will be described below, and a series of oblong shaped holes 134 along the middle shaft 130.

The outer sleeve 140 includes a handle 141 at the proximal end, threads 142 on the inner surface at the proximal end, a series of oblong shaped holes 143 below the handle 141 on the shaft, and a chamfered cut 144 at the inner edge of the distal end of the sleeve.

Figure 14:
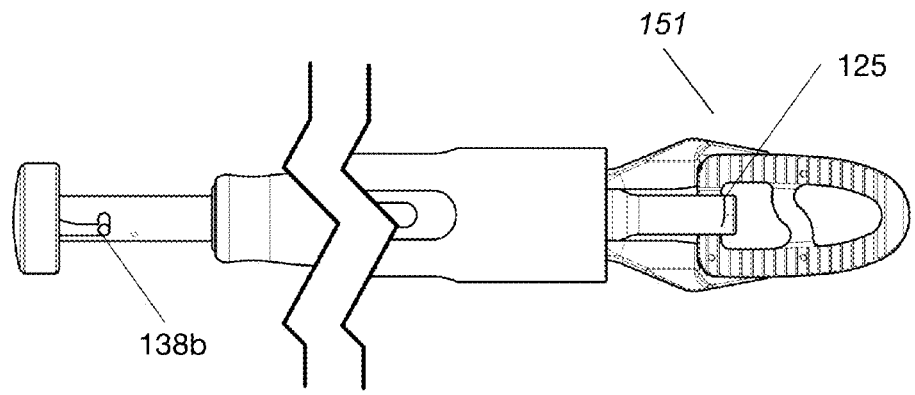
FIG. 14 shows the implant assembly with the inserter tool attached to the implant in the unlocked position.
Figure 15:
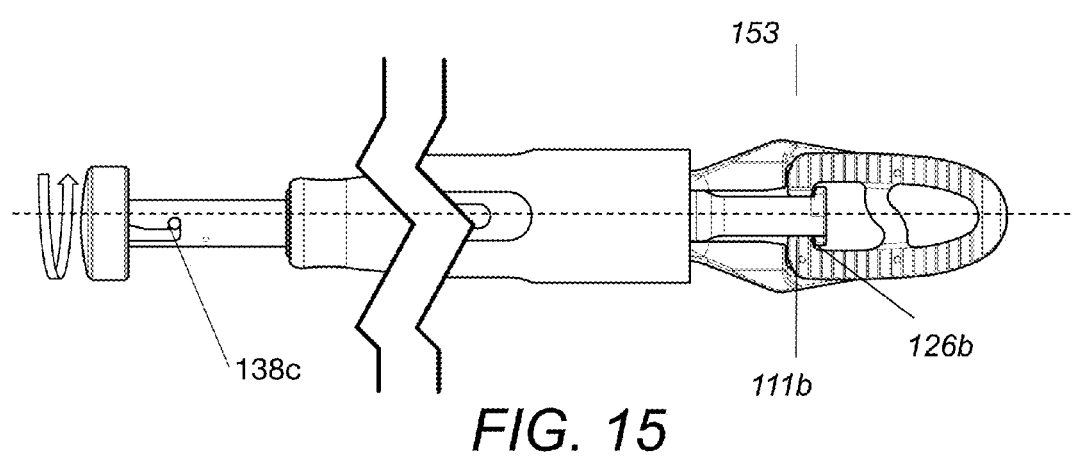
FIG. 15 shows the implant assembly with the inserter tool attached to the implant in the locked position.
Figure 16:
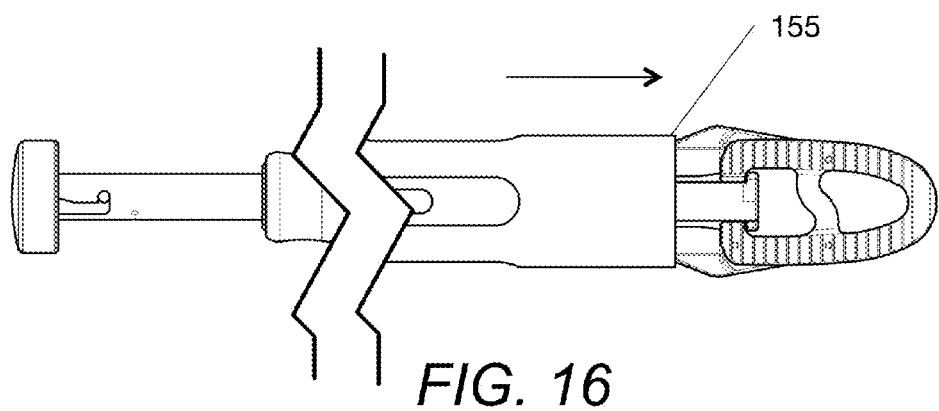
FIG. 16 shows the implant assembly with the outer sleeve of the inserter tool in the locked position.

FIG. 14-16 depict the mechanism of attaching and locking the inserter 120 to the implant 100. Referring to FIG. 14, protrusions 136a and 136b of the attachment jaws 135 of the middle shaft 130 slide into the side grooves 108 of the implant 100 and then the flat disc 125 of the inner shaft 121 is inserted into the open back end 102 of the implant 100 and protrusions 126a, 126b are placed into openings 118a, 118b of the back end of the implant 100. In the unlocked position 151, the flat disc 125 is placed in the back end 102 and the notch 123 at the proximal end of the inner shaft 121 is at the left corner 138b of the L-shaped opening 131 on the middle shaft 130. Referring to FIG. 15, the inner shaft is rotated by a quarter turn and the flat disc 125 is now in the locked position 153 with the flat disc protrusions 126a, 126 being behind the vertical walls 113a, 113b of extensions 111a, 111b, respectively. The notch 123 at the proximal end of the inner shaft is now at the right corner 138c of the L-shaped opening 131 of the middle shaft 130. Referring to FIG. 16, the handle 141 of the outer sleeve 140 is rotated to screw the inner thread 144 of the outer sleeve onto the outer threads 133 of the middle sleeve 130 and in this way the outer sleeve 140 travels downward along direction 155 over the middle sleeve 130 to cover a portion of the attachment jaws 135 and thereby to prevent the attachment jaws 135 from spreading outward. This step fully secures the implant 100 onto the inserter 120. These steps are reversed to release the implant 100 from the inserter 120. The inserter is easily disassembled without any special tools, by first overcoming the detent hole mechanism 132 and the spring-loaded ball 124 and then pulling the inner shaft 121 out of the middle sleeve 130. The outer sleeve 140 is then unscrewed from the inner shaft 121 and this completes the disassembly of the inserter tool.

Figure 17A:
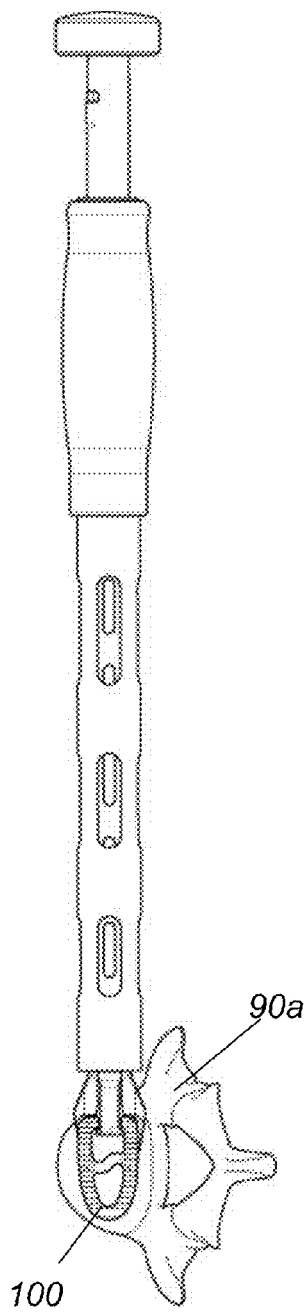
FIG. 17a shows an axial view of a vertebra with the inserter tool and the implant in the implanted position.
Figure 17B:
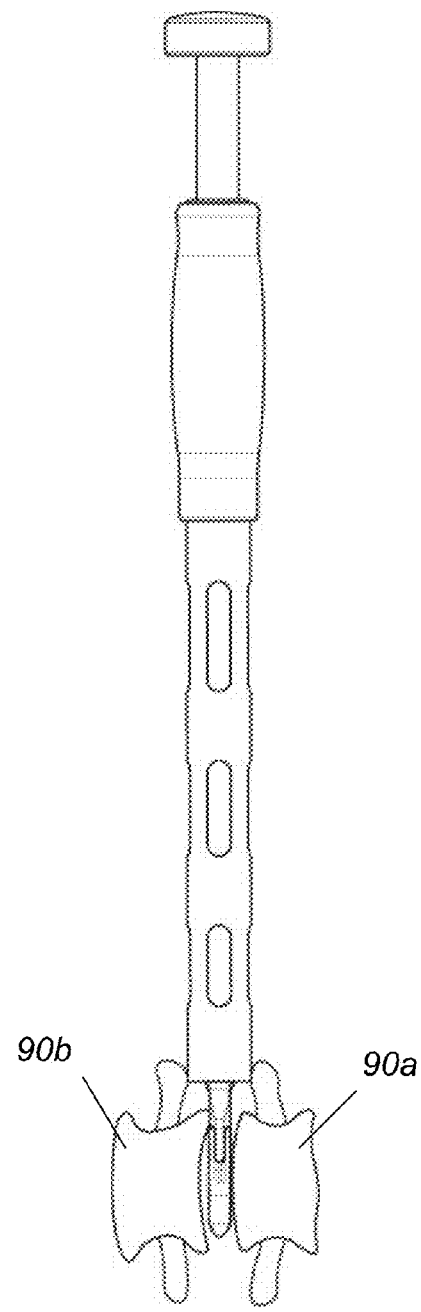
FIG. 17b shows an anterior view of two adjacent vertebras with the inserter tool and the implant in the implanted position.

Referring to FIG. 17a and FIG. 17b, in operation, the implant 100 is inserted into the body and placed in between two adjacent vertebrae 90a, 90b. The inserter 120 enters the body from the side along a medial direction.

Several embodiments of the present invention have been described. Nevertheless, it will be understood that various modifications may be made without departing from the spirit and scope of the invention. Accordingly, other embodiments are within the scope of the following claims.

What is claimed is:
1. An intervertebral implant assembly for stabilization and decompression of two adjacent spinal vertebras, comprising:
an implant having a U-shaped body shaped and dimensioned to be placed between two adjacent vertebras, wherein said U-shaped body comprises a rounded front end, an open back end, first and second elongated components extending from the rounded front end, forming the U-shaped body and ending at the open back end and at least one S-shaped rigid strut extending from and connecting opposite inner side surfaces of the first and second elongated components;
a first through-opening formed in the space between the front end, the rigid strut and the opposite inner side surfaces of the front portions of the first and second elongated components; a second through-opening formed in the space between the open back end, the rigid strut and the opposite inner side surfaces of the back portions of the first and second elongated components; and
wherein top and bottom surfaces of the U-shaped body are inclined and taper from an outer side surface of the first elongated component toward an outer side surface of the second elongated component;
wherein the first and second elongated components comprise first and second extensions, extending from and being perpendicular to the back ends of the first and second elongated components, respectively, and wherein said first and second extensions protrude inward and do not converge together;
wherein the first extension comprises a first rectangular portion at the bottom, a rounded portion in the middle and a second rectangular portion at the top, wherein the second rectangular portion is set outward relative to the first rectangular portion at a plane parallel to the first rectangular portion; and
wherein the second extension comprises a first rectangular portion at the top, a rounded portion in the middle and a second rectangular portion at the bottom, wherein the second rectangular portion is set outward relative to the first rectangular portion at a plane parallel to the first rectangular portion.

2. The assembly of claim 1 further comprising first and second grooves formed on the outer side surfaces of the first and second elongated components and wherein said first and second grooves start at the back end and terminate at the mid-section of the outer side surfaces of the first and second elongated components, respectively.

3. The assembly of claim 1 wherein top and bottom surfaces of the U-shaped body comprise protrusions configured to grip into the bottom and top surfaces of the two adjacent vertebras, respectively.

4. The assembly of claim 1 wherein said U-shaped body further comprises holes extending from the top surface to the bottom surface and pins dimensioned to fit within the holes and wherein the pins comprise radio-opaque material and are used as position indicators during fluoroscopy.

5. The assembly of claim 1 further comprising bone growth material inserted in the first and second through openings.

6. An intervertebral implant assembly for stabilization and decompression of two adjacent spinal vertebras, comprising:
an implant having a U-shaped body shaped and dimensioned to be placed between two adjacent vertebras, wherein said U-shaped body comprises a rounded front end, an open back end, first and second elongated components extending from the rounded front end, forming the U-shaped body and ending at the open back end and at least one rigid strut extending from and connecting opposite inner side surfaces of the first and second elongated components;
wherein the first and second elongated components comprise first and second extensions, extending from and being perpendicular to the back ends of the first and second elongated components, respectively, and wherein said first and second extensions protrude inward;
a first through-opening formed in the space between the front end, the rigid strut and the opposite inner side surfaces of the front portions of the first and second elongated components; and
a second through-opening formed in the space between the open back end, the rigid strut and the opposite inner side surfaces of the back portions of the first and second elongated components;
wherein the first and second elongated components comprise first and second extensions, extending from and being perpendicular to the back ends of the first and second elongated components, respectively, and wherein said first and second extensions protrude inward and do not converge together;
wherein the first extension comprises a first rectangular portion at the bottom, a rounded portion in the middle and a second rectangular portion at the top, wherein the second rectangular portion is set outward relative to the first rectangular portion at a plane parallel to the first rectangular portion;
wherein the second extension comprises a first rectangular portion at the top, a rounded portion in the middle and a second rectangular portion at the bottom, wherein the second rectangular portion is set outward relative to the first rectangular portion at a plane parallel to the first rectangular portion;

an inserter tool, wherein said inserter tool comprises:

an elongated inner shaft extending along a first direction and comprising a flat disc component at the distal end, wherein the flat disc component extends perpendicular to the first direction and comprises first and second protrusions extending from the sides of the flat disc component and wherein said first and second protrusions are configured to be inserted in the open back end of the U-shaped body and to be placed behind the first and second extensions of the first and second elongated components, respectively;

a middle sleeve surrounding the elongated shaft and comprising an attachment jaw at its distal end and an L-shaped opening at its proximal end;

an outer sleeve surrounding the middle sleeve; and wherein said first and second extensions are used for locking the implant onto said inserter tool via a twist locking mechanism.

7. The assembly of claim 6 wherein the elongated inner shaft further comprises a pin at its proximal end wherein said pin is shaped and dimensioned to be inserted and rotated within the L-shaped opening of the middle sleeve.

8. The assembly of claim 6 wherein the elongated inner shaft further comprises a spring-loaded ball and the middle sleeve comprises first and second detent holes dimensioned to capture said spring loaded ball.

9. The assembly of claim 6 wherein said attachment jaw comprises first and second protrusions shaped and dimensioned to slide within first and second grooves of the U-shaped body, respectively.

10. The assembly of claim 9 wherein said first and second protrusions comprise ridges on their inner surfaces.

11. The assembly of claim 9 wherein said outer sleeve comprises inner threads and said middle sleeve comprises outer threads and wherein said outer sleeve inner threads are configured to engage the outer threads of the middle sleeve and thereby to move the outer sleeve partially over the attachment jaw and thereby to lock the first and second protrusions in place.

* * * * *